(12) United States Patent
Lloyd et al.

(10) Patent No.: US 8,709,462 B2
(45) Date of Patent: Apr. 29, 2014

(54) TERMITE TUBING PREVENTATIVE FOR NON-WOOD MATERIALS

(75) Inventors: Jeffrey Douglas Lloyd, Knoxville, TN (US); Ronald Thomas Schwalb, Knoxville, TN (US)

(73) Assignee: Nisus Corporation, Rockford, TN (US)

( * ) Notice: Subject to any disclaimer, the term of this patent is extended or adjusted under 35 U.S.C. 154(b) by 568 days.

(21) Appl. No.: 12/479,905

(22) Filed: Jun. 8, 2009

(65) Prior Publication Data
US 2009/0301000 A1 Dec. 10, 2009

Related U.S. Application Data

(63) Continuation of application No. 10/758,987, filed on Jan. 16, 2004.

(51) Int. Cl.
*A01N 25/08* (2006.01)

(52) U.S. Cl.
USPC ........... 424/411; 424/405; 424/658; 424/659; 424/660; 424/DIG. 11

(58) Field of Classification Search
None
See application file for complete search history.

(56) References Cited

U.S. PATENT DOCUMENTS

| | | | |
|---|---|---|---|
| 4,610,881 | A | 9/1986 | Bechgaard |
| 5,104,664 | A | 4/1992 | Palmere et al. |
| 5,296,240 | A | 3/1994 | Palmere et al. |
| 5,346,699 | A | 9/1994 | Tiernan |
| 5,592,774 | A | 1/1997 | Galyon |
| 6,368,529 | B1 | 4/2002 | Manning et al. |
| 6,423,251 | B1 | 7/2002 | Blount |
| 6,426,095 | B2 | 7/2002 | Palmere et al. |
| 6,630,174 | B2 | 10/2003 | Palmere et al. |
| 6,667,350 | B1 | 12/2003 | Satula |
| 6,881,147 | B2 | 4/2005 | Batdorf |
| 6,881,247 | B2 | 4/2005 | Batdorf |

(Continued)

FOREIGN PATENT DOCUMENTS

| | | |
|---|---|---|
| AU | 2003203735 | 4/2003 |
| DE | 101 32 532 | 2/2003 |

(Continued)

OTHER PUBLICATIONS

Nisus Original Complaint, Filed Mar. 19, 2010.

(Continued)

*Primary Examiner* — Neil Levy
(74) *Attorney, Agent, or Firm* — Luedeka Neely Group, P.C.; J. David Gonce

(57) ABSTRACT

The present invention relates to materials and methods for protecting man-made structures made with non-wood materials from termite damage through the application of borates to the surface of non-wood materials. In an embodiment the invention regards a method for preventing termite tunneling and tubing on non-wood and/or non-cellulosic materials by treating non-wood building components comprising the steps of applying a composition to the surfaces of a non-wood building component, wherein the composition comprises a borate component. In another embodiment the invention regards a method for preventing termite damage to man-made structures comprising the steps of mixing borates with a solvent to form a borate solution, obtaining a non-wood building component, coating the non-wood building component with the borate solution, and incorporating the coated non-wood building component into a man-made structure. The invention also regards a non-wood building component comprising a non-wood substrate, and a coating comprising borates, wherein the coating is disposed on the surfaces of the non-wood substrate.

10 Claims, 2 Drawing Sheets

(56) References Cited

U.S. PATENT DOCUMENTS

| | | |
|---|---|---|
| 6,896,908 B2 | 5/2005 | Lloyd et al. |
| 7,163,974 B2 | 1/2007 | Manning et al. |
| 7,223,415 B1 | 5/2007 | Malone et al. |
| 2003/0068485 A1 | 4/2003 | Ramsey |
| 2007/0122442 A1 | 5/2007 | Lloyd et al. |

FOREIGN PATENT DOCUMENTS

| | | |
|---|---|---|
| EP | 0248991 | 12/1987 |
| JP | 62-195301 | 8/1987 |
| JP | H1-318071 | 12/1989 |
| JP | 2000-063202 | 2/2000 |
| JP | 2001-200088 | 7/2001 |
| JP | 2001-220834 | 8/2001 |
| JP | 2001-220837 | 8/2001 |
| WO | WO92 22205 | 12/1992 |
| WO | WO95 35029 | 12/1995 |
| WO | WO00 11948 | 3/2000 |
| WO | WO0015033 | 3/2000 |
| WO | WO0117348 | 3/2001 |
| WO | WO01 87559 | 11/2001 |

OTHER PUBLICATIONS

Nisus Amended Complaint, Filed Apr. 28, 2010.
Sostram's Redacted Answer and Counterclaim, Filed Jun. 17, 2010.
Bora-Care Technical Bulletin, 2003.
Product Label for Bora-Care, Apr. 2001.
"Ecopowder BX" Instruction and Application Manual for Termite Repelling and Preservation, Ecopowder Corporation, Feb. 27, 2003.

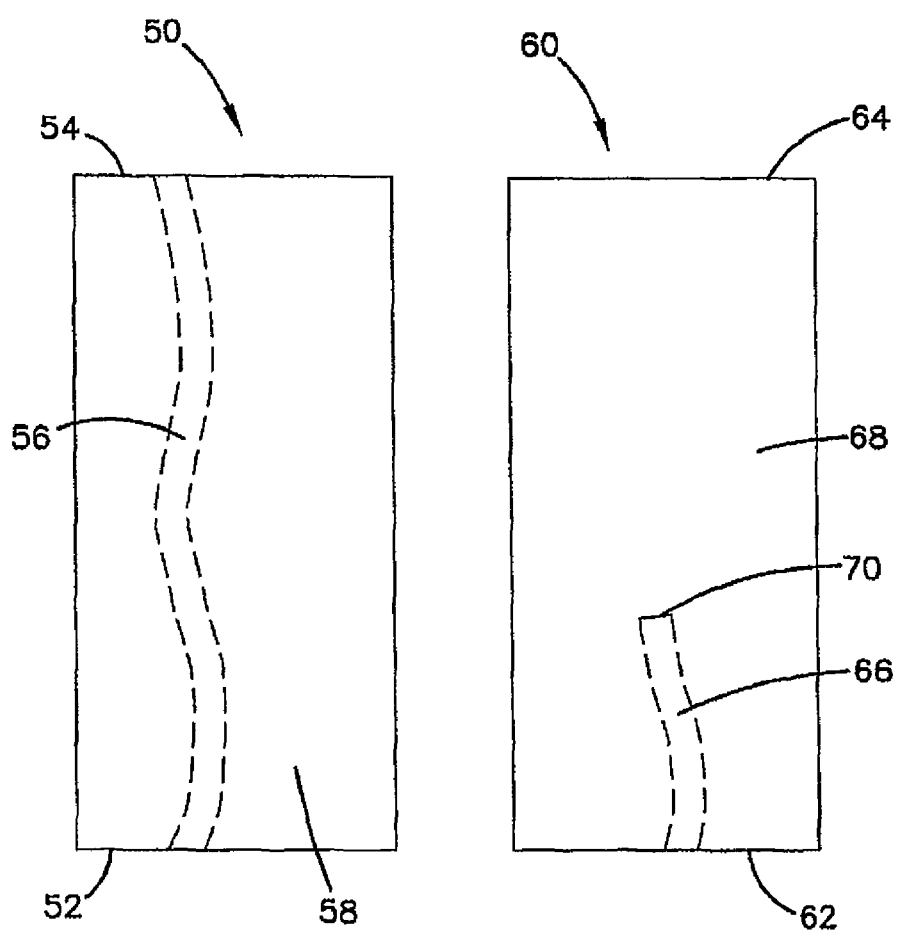

TERMITE TUBING PREVENTATIVE FOR NON-WOOD MATERIALS

This application is a continuation of copending application Ser. No. 10/758,987, filed Jan. 16, 2004.

FIELD OF THE INVENTION

The present invention relates to materials and methods for protecting man-made structures from termite damage by treating non-wood and/or non-cellulosic materials. More particularly, the present invention relates to the application of borates to the surface of non-wood and/or non-cellulosic materials.

BACKGROUND OF THE INVENTION

Termites are unique among insects in their ability to derive nutritional benefit from cellulose, which is the component of wood and plants that gives structural rigidity to cells. However, as a result of feeding on wood and cellulose containing products, termites can cause significant damage to man-made structures and the cellulose materials contained within.

Generally speaking, subterranean termites must stay in close reach of the soil at all times, lest they die from dehydration. Accordingly, wood touching soil is easily accessed and damaged by termites. However, subterranean termites also can build shelter tubing to travel between the soil and wood that is nearby, but not actually touching the soil. The shelter tubing provides a dark, moist environment that protects the termites from sunlight, predators, or dehydration. Termites may also build shelter tubes through the soil to avoid certain highly repellant termiticides.

To prevent termite damage, termite barrier insecticides have been applied to soil under and around dwellings for many years as a chemical barrier. Approaches have included the injection or spray application of large volumes of organic pesticides such as organophosphates and pyrethroids into soil prior to the pouring or construction of building foundations. However, this approach causes environmental concerns as the pesticide goes directly into the environment. Moreover, this approach has performance limitations because the pesticide is lost from the vicinity within a 3 to 10 year period, thereafter allowing termite access. Further, rain during construction or some other form of physical activity (digging, walking, pipe laying etc) breaks the barrier and often leads to premature failure of the insecticide treatment.

A different approach to termite control has been to apply borates to wood used in construction through spray or pressure applications to poison the termites' food source. Borates have been used in almost all types of wood end use including the treatment of solid wood, plywood and wood composites. The benefits of borates include efficacy against all wood destroying organisms (fingi, boring beetles & termites), low acute mammalian toxicity and low environmental impact. As an example of this approach, a specific glycol borate formulation containing 40 wt. % disodium octaborate tetrahydrate (DOT) and applied diluted in water to 23 wt. % DOT (available commercially as BORA-CARE®), has been demonstrated and approved in the USA as a stand alone alternative to soil poisoning, when sprayed on all structural wood to a height of two feet in new construction.

However, treating only structural wood with borates has practical limitations. One limitation of this approach is that a large percentage of new construction uses building materials other than wood. Brick, block, concrete, steel frame, vinyl, stucco, gypsum, expanded foam and polystyrene board are all common construction materials that can be used in the absence of wood, or with a very low volume of wood. While termites generally don't directly damage non-cellulosic materials such as concrete, termites have the ability to build shelter tubing over these non-wood construction materials and then cause damage to books, paper, wall coverings, wood composite fixtures and fitting, hardwood floors, and other wood or cellulose items. Thus, while it is not effective to treat homes and commercial building constructed in this way by treating only structural wood with borates, subterranean termite protection is still warranted.

Another approach to the use of borates has been to incorporate them into building products, including cementitious products. However, this approach has not proven effective as it still allows termite tubing over the building material so the terminates can reach other vulnerable items. This approach has a further limitation in that the application of borates to cementitious products may act as a setting retardant and ultimately affect structural integrity of some building products into which it is incorporated.

Therefore, a need exists for an environmentally safer way of protecting man-made structures made with non-wood materials, and the contents therein, from termite damage.

SUMMARY OF THE INVENTION

In an embodiment the invention regards a method for preventing termite tunneling and tubing on non-wood and/or non-cellulosic materials by treating non-wood building components comprising the steps of applying a composition to the surfaces of a non-wood building component, wherein the composition comprises a borate component. In another embodiment the invention regards a method for preventing termite damage to man-made structures comprising the steps of mixing borates with a solvent to form a borate solution, obtaining a non-wood building component, coating the non-wood building component with the borate solution, and incorporating the coated non-wood building component into a man-made structure. The invention also regards a non-wood building component comprising a non-wood substrate, and a coating comprising borates, wherein the coating is disposed on the surfaces of the non-wood substrate.

The above summary of the present invention is not intended to describe each discussed embodiment of the present invention. This is the purpose of the figures and the detailed description that follows.

DRAWINGS

The invention may be more completely understood in connection with the following drawings, in which:

FIG. 2 is an example of termite tubing behavior on a non-wood building component with a borate solution coating and on a non-wood building component without a borate solution coating.

Figure 1:
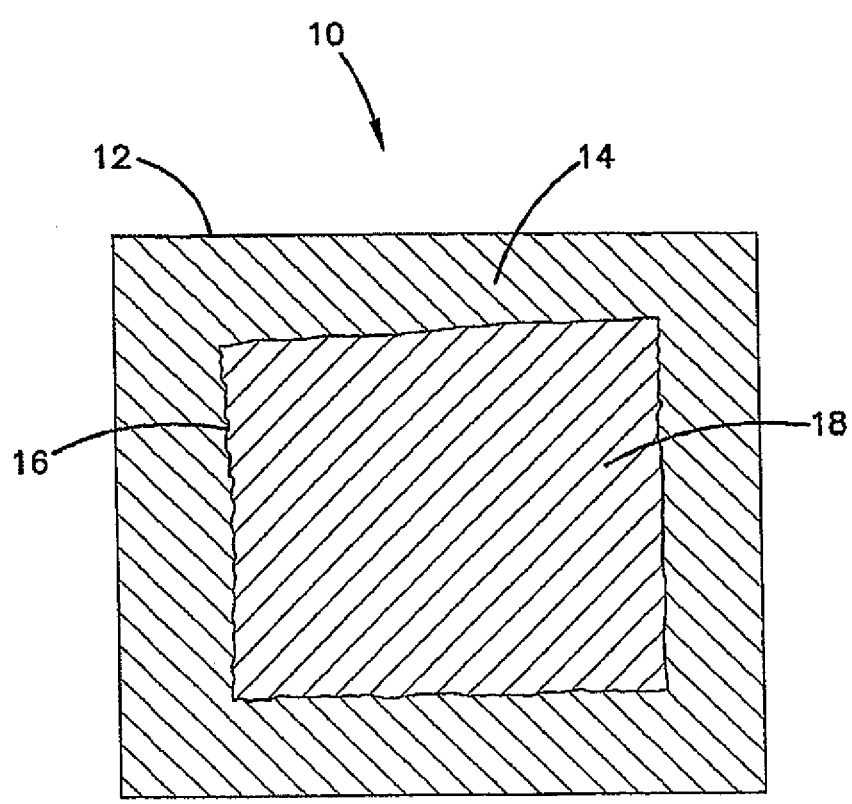
FIG. 1 is a cross-section of a non-wood building component with a borate solution coating.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Where a borate composition is applied to a non-wood substrate in accordance with the invention, termites attempt to form tubes, but there is very rapid termite mortality and therefore a discontinuation of tubing activity on the treated non-wood substrates.

In an embodiment the invention regards a method for preventing termite tunneling and tubing on non-wood and/or non-cellulosic materials by treating non-wood building components comprising the steps of applying a composition to the surfaces of a non-wood building component, wherein the composition comprises a borate component. In another embodiment the invention regards a method for preventing termite damage to man-made structures comprising the steps of mixing borates with a solvent to form a borate solution, obtaining a non-wood building component, coating the non-wood building component with the borate solution, and incorporating the coated non-wood building component into a man-made structure. The invention also regards a non-wood building component comprising a non-wood substrate, and a coating comprising borates, wherein the coating is disposed on the surfaces of the non-wood substrate.

Materials to be Treated

Many different non-wood and/or non-cellulosic materials can be treated with a borate composition in accordance with various embodiments of the invention. For example, in an embodiment, cementitious materials are treated. Cementitious materials are those materials that are made from cement and/or have the properties of cement. Suitable materials for treatment can include brick, block, stone, concrete, stucco, gypsum. Metals can also be treated with a borate composition in accordance with the invention. For example, steel or copper may be treated. Additionally, plastics or polymeric based materials can be treated including expanded foam, PVC, vinyl, polystyrene and other plastics or polymers. One of skill in the art will appreciate that many non-wood and/or non-cellulosic substrates can be treated in accordance with the invention.

Materials of varying levels of porosity may be treated in accordance with the invention. In some embodiments, materials with a high level of porosity are treated. In other embodiments, materials that have a less than high level of porosity are treated.

Borate Compositions Applied

The borate compositions applied may comprise a borate compound as an active agent, a carrier, and a diluent. One of skill in the art will appreciate that the borate compositions applied may also comprise other components including adjunct active agents, solubility enhancers, colorings or dyes, co-diluents, viscosity modifying agents, adhesive components, powders, polymer forming agents, etc. In an embodiment, the borate compositions applied may comprise a dry composition, depending on the nature of building component to be treated. The form of the borate composition may vary depending on the type of material treated, the termite species from which protection is desired, and the ambient climatic conditions.

Suitable borate compounds may include those of high or low solubility. Low solubility borate compounds may be used in the form of a suspension, may be treated first to enhance their solubility, or may be used in conjunction with a separate compound that functions to enhance their solubility. Suitable borate compounds may include boric acid, sodium borates such as borax and DOT (disodium octaborate tetrahydrate), zinc borates, calcium borates, sodium calcium borates, calcium magnesium borates, organic borates such as boresters and boronic acids and any mixtures thereof. Suitable carriers may include polyalkylene glycols, including short chain polyalkylene glycols having an average molecular weight of between about 100 and 500. Specific carriers include propylene glycol, monoethylene glycol, diethylene glycol, triethylene glycol and polyethylene glycol. Suitable diluents include polar solvents such as water, alcohols or glycols, with or without the addition of surfactants. Organic solvents such as mineral spirits and kerosene can be used with emmulsifiers or with organic borates such as boresters or boronic acids. Other components such as rheology modifiers, thickening agents and polymerizing film formers such as starch, agar, xanthan gum, gelatin, latex, acrylics, alkyds etc., may also be added.

The borate composition, as it is applied, may not work optimally if it comprises too low of a concentration of a borate compound. Therefore, in some embodiments, the borate composition comprises greater than 0.1 wt % of a borate compound. In a particular embodiment, the borate composition comprises between 0.1 wt % and 100.00 wt % of a borate compound. In another embodiment, the borate composition may comprise between about 10.0 wt % and 30.0 wt % of a borate compound.

In one embodiment the borate composition comprises glycol, DOT (disodium octaborate tetrahydrate), and water, wherein the DOT ranges from 10.0 wt % to 30.0 wt %. As an example, a solution of glycol, DOT (disodium octaborate tetrahydrate), and water is commercially available, sold as BORA-CARE®, and is available from Nisus Corporation, 100 Nisus Drive, Rockford, Tenn. 37853. Glycols are readily available from a variety of commercial sources. One such source is Dow Chemical. For example, E200 is an ethylene glycol having an average molecular weight of about 200 and a chemical abstract registry number of 25322-68-3 and is available from Dow Chemical.

Borate Application

The borate solution may be applied by a number of different methods including low pressure spraying, high pressure spraying, brushing, dipping, misting, foaming, fogging, roller coating, spreading, pressure immersion and even gaseous application. Where gaseous application is employed, volatile borates, such as boresters including trimethyl borate, may be used. The specific application technique used may vary with the given material treated. In many embodiments, the borate solution is applied after the building component, or substrate, is already formed, as opposed to mixing the borate solution into the material before the building component is formed.

The borate solution may be applied to the interior, and or exterior walls of a ready-built, or partially built, structure. The borate solution may also be applied to cavities of a ready built structure (e.g. cavity wall or within hollow concrete blocks). The borate solution may also be applied to the concrete slab or foundation walls of new or existing structures. The borate solution may be applied in and around bath traps or other areas where external utilities (water pipes, electric conduits, gas pipes etc) are brought into a structure.

The total amount of borates to be applied depends on the particular substrate as well as the particular insect species from which protection is sought. A coating without a sufficient amount of borates may not be optimal. In an embodiment, a coating that is greater than 0.005 g/cm$^2$ of a borate solution is applied. However, using more borates than is necessary for sufficient performance may be uneconomical. Therefore, in an embodiment, a coating that is less than 1.0 g/cm$^2$ of a borate solution is applied. In an embodiment, an average coating of from about 0.005 g/cm$^2$ to about 1 g/cm$^2$ of borate solution is applied. In another embodiment, an average coating of from 0.04 g/cm$^2$ to 0.10 g/cm$^2$ of borate solution is applied. In a particular embodiment, an average coating of 0.071 g/cm$^2$ of borate solution is applied.

As many non-wood building components are porous, application of a borate composition will lead to some penetration of the solution into the building component. Penetration, in effect, depletes protection by reducing the surface concentration of borates. In many non-porous materials penetration is minimal. Penetration may also be limited in dry porous materials. The depth of penetration will depend on the particulars of the borate composition as well as the given building component including its porosity and moisture content, in addition to the mode of borate application. Generally, borate compositions with higher levels of light organic solvents will penetrate more deeply into a given dry building component.

Referring to FIG. 1, a cross-sectional view of a building component 10 is shown that has been treated with a borate composition. The borate composition has been applied to the surface 12 of the building component 10 and has penetrated throughout a penetration zone 14 (not drawn to scale) around the perimeter of the building component 10. The borate composition has penetrated to the edge 16 of the penetration zone, dividing the penetration zone 14 from an exclusionary zone 18 on the interior of the building component. While FIG. 1 shows a penetration zone 14, one of skill in the art will appreciate that at least where a non-porous or only slightly porous building components are used, a penetration zone may not be formed and the borate composition may reside at the surface of the building component.

In an embodiment of the invention, the borate composition is a low solubility borate applied in a non-solubilizing and/or highly volatile solvent, in order to limit penetration and maximize the amount of the borate composition available at the surface of the building product. Other methods of limiting borate penetration are also contemplated by the invention. By way of example, a penetration minimizing solution can be applied to the non-wood building component before the borate solution is applied. Such a penetration minimizing solution can act to fill the pores of the non-wood building component such that when the borate solution is later applied it does not filter into the component as deeply. Examples would include wax emulsions, polymer forming agents such as polyvinyl alcohol, silicone, acrylics, alkyds or other sealants such as coating systems or paints. In an embodiment, the invention comprises a coating of a penetration minimizing agent.

Insects

Embodiments of the invention are effective in preventing damage from subterranean termites including *Reticulitermes, Heterotermes, Coptotermes, Microtermes, Nasutitermes, Neotennes* and *Mastitermes*. The invention, in one embodiment, may be effective against *Reticulitermes, Heterotermes* and *Coptotennes* termites in particular. In a particular embodiment, the invention can be used to prevent damage caused by Formosan subterranean termites (*Coptotermes formosanus*). In other embodiments, the invention is used to prevent damage from tube forming insects generally, such as mud daubing wasps.

The present invention may be better understood with reference to the following examples. These examples are intended to be representative of specific embodiments of the invention, and are not intended as limiting the scope of the invention.

Example 1

Application of Borates

Concrete decorative columns, 15.2 cm×5 cm×61 cm (6 inches×2 inches×24 inches) with one scalloped edge, were obtained as exemplary non-wood building components. The columns were given a brush treatment with a solution comprising 20 wt. % disodium octaborate tetrahydrate, a glycol carrier, and water on all surfaces of the columns to the point of surface refusal.

An average coating of 0.071 g/cm$^2$ of the solution was applied as shown in Table 1. The treatments were cured at room temperature prior to testing.

TABLE 1

|  | Treatment Weight | Surface Area | g/cm2 |
| --- | --- | --- | --- |
| Column 1 | 161.05 | 2274 | 0.0708 |
| Column 2 | 161.06 | 2274 | 0.0708 |
| Column 3 | 160.96 | 2274 | 0.0708 |
| Column 4 | 161.33 | 2274 | 0.0710 |
| Column 5 | 162.53 | 2274 | 0.0715 |

Example 2

Tubing Test

The five treated columns from Example 1 (columns 1-5) were tested against 5 otherwise identical untreated columns (columns 6-10). The test also included a southern yellow pine control to determine general termite activity. Each concrete column was placed on edge to provide a column that extended 58.4 cm (23 inches) above the sand surface. Each column was placed in 1500 grams of autoclaved blasting sand containing 300 grams of distilled water. A piece of southern yellow pine sapwood was placed on top of each column. Formosan subterranean termites (*Coptotermes formosanus*) were collected by a bait crate method from Brechtel State Park in Louisiana. These are recognized as the most voracious, most damaging and most difficult to control of the subterranean termites. Two thousand Formosan subterranean termites (determined by weight from sampling) were placed on the sand in the pan. This structure was placed in a larger pan to create a moat to keep the termites from escaping. Each setup was covered by plastic bags to maintain high humidity. The southern yellow pine controls were used to determine health and quality of the termites. Where applicable, testing followed the standard as described in American Wood-Preservers' Association Standard E1-97. All tests were maintained in a conditioned room at 27° C.

An initial test for a concrete control (Column #7) was set up to determine if the termites would tunnel on the concrete. After 4 days a tunnel had been constructed 16 inches above the sand level. The southern yellow pine controls were set up and run for 28 days. The visual rating for the controls was based on the following rating system: 10—Sound, surface nibbles permitted; 9—Light attack; 7—Moderate attack, penetration; 4—Heavy attack; 0—Failure.

Example 3

Effectiveness in Preventing Tubing

The concrete column test was run for 30 days. The columns were initially checked daily with the length of any tubing present and the number of termites found in the surrounding water noted. The results for the tubing activity are shown in Table 2. In these tables, treated columns are numbered 1-5 and the untreated columns numbered 6-10.

The tubing activity was measured every day for the first 18 days. It was found that termites built tubes the entire length of the column in only 1 to 7 days for the untreated columns, once tubing started. Termites on the borate treated columns reacted differently. The Formosan subterranean termites in these setups were not able to produce tubes over 20 cm (8 inches) in length with one reaching a total height of only 10 cm (4 inches). On two of the five treated columns, the initial tube on the flat edge of the column was abandoned and new tubes were started on the scalloped side of the column. These tubes failed as well. Termites took an average of less than 8 days to complete their tube from the sand to the top of the column on untreated columns. However, they could only reach an average height of 16.5 cm (6.5 inches) in 8 days on treated columns with no further progress beyond that point.

The quality of the tubes also varied. The tubes on the untreated columns appeared strong and durable whereas the tubes on the treated columns were weak and crumbly. The tubes on the treated columns were not maintained. In the end, some deterioration was found on all southern yellow pine blocks, whether the column was treated or not. Deterioration was much more severe on the wood supported on the untreated columns. While not intending to be bound by theory, it is believed that some deterioration was observed on the treated columns because with no alternative food source in the experiment, the termites ultimately crossed the column to the food source even without tubes and were able to do this as the test units were enclosed in plastic bags to maintain high humidity. It is believed that this would not happen in nature where alternative food sources are inevitably available and where only tubes will prevent dehydration and death.

Referring to FIG. 2, examples of tubing behaviors on columns with and without borate solution coatings are shown. On an exemplary uncoated column 50, termites form a tube 56 on the surface 58 of the uncoated column 50 starting from the base 52 of the uncoated column 50 to the top 54 of the uncoated column 50. In contrast, on a coated column 60, termites begin to form a tube 66 on the surface 68 of the coated column starting from the base 62, but the tube 66 is terminated at a point 70 that is before the top 64 of the coated column.

Example 4

Termite Mortality

Termites were found in the water surrounding the setup on a daily basis. These termites were collected and counted providing a daily mortality count. As can be seen in Table 3, there was a significantly larger number of termites that were in the water from the treated columns than the untreated. The treated concrete had an average of 799 termites in the water over the 30 day period or 40% mortality of the original number placed in the test. The mortality of termites used in the untreated concrete test averaged a total of 93 termites or 4.7% mortality. Mortality of the termites on the untreated column due to drowning decreased considerably once the tube reached the top of the column. Mortality of the termites on the treated columns caused by drowning was very high sometimes reaching more than 50% in two weeks on individual columns.

A summary of the test breakdown data is provided in Table 4. Data consists of total termite mortality (water mortality plus other) for the concrete column setups and mortality, weight loss, and visual rating for the southern yellow pine block controls in the jar test. As can be seen in this table, there were very high mortality rates for the treated concrete column setup averaging 92.7%, moderate mortality for the untreated columns averaging 35.7%, and low mortality for the pine controls averaging 13.2%. In addition, the higher weight loss for the controls (43.7%), combined with the low ratings (0.8) indicated that the termites were healthy and very active. As shown in Table 4, the very high mortality rate for the treated columns indicates that the treatment also caused death of termites in the sand as well as death by drowning.

TABLE 2

| Col. # | Beginning Date | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|
| 1 | Aug. 26, 2003 | 0 | 0.5 | 1.5 | 3.75 | 3.75 | 3.75 | 8 | 8 | 0 | 0 | 0 | 0 | 0 | 0 |
| 2 | Aug. 26, 2003 | 0 | 0.5 | 0.5 | 0.5 | 0.5 | 0.5 | 4 | 4 | 0 | 0 | 0 | 0 | 0 | 0 |
| 3 | Aug. 26, 2003 | 0 | 0 | 1.5 | 5 | 5 | 5 | 6.5 | 6.5 | 0 | 0 | 0 | 0 | 0 | 0 |
| 4 | Aug. 26, 2003 | 0 | 0 | 2 | 5 | 5 | 5 | 7 | 7 | 0 | 0 | 0 | 0 | 0 | 0 |
| 5 | Aug. 26, 2003 | 0 | 0 | 3.75 | 6 | 6 | 6 | 8 | 8 | 0 | 0 | 0 | 0 | 0 | 0 |
| 6 | Aug. 26, 2003 | 0 | 3.5 | 9 | 18 | 18 | 18 | 23 | top | top | top | top | top | top | top |
| 7 | Aug. 22, 2003 | 7 | 7.5 | 16 | 23 | top | top | top | top | top | top | top | top | top | top |
| 8 | Aug. 26, 2003 | 0 | 0 | 0 | 0 | 0 | 18.5 | 23 | top | top | top | top | top | top | top |
| 9 | Aug. 28, 2003 | 0 | 0 | 0 | 0 | 0 | 0 | 0 | 0 | 0 | 0 | 0 | 0 | 0 | 0 |
| 10 | Aug. 26, 2003 | 0 | 0 | 0 | 0 | 0 | 0 | 23 | 100 | 0 | top | top | top | top | top |

| Col. # | Day 16 | Day 17 | Day 18 | Day 19 | Day 20 | Day 21 | Day 22 | Day 23 | Day 24 | Day 25 | Day 26 | Day 27 | Day 28 | Day 29 | Day 30 |
|---|---|---|---|---|---|---|---|---|---|---|---|---|---|---|---|
| 1 | 0 | 0 | 0 | NM | NM | 0 | 0 | 0 | 0 | 0 | NM | NM | 0 | 0 | 0 |
| 2 | 0 | 0 | 0 | NM | NM | 0 | 0 | 0 | 0 | 0 | NM | NM | 0 | 0 | 0 |
| 3 | 0 | 0 | 0 | NM | NM | 0 | 0 | 0 | 0 | 0 | NM | NM | 0 | 0 | 0 |
| 4 | 0 | 0 | 0 | NM | NM | 0 | 0 | 0 | 0 | 0 | NM | NM | 0 | 0 | 0 |
| 5 | 0 | 0 | 0 | NM | NM | 0 | 0 | 0 | 0 | 0 | NM | NM | 0 | 0 | 0 |
| 6 | top | top | top | NM | NM | top | top | top | top | top | NM | NM | top | top | top |
| 7 | top | top | top | NM | NM | top | top | top | top | top | NM | NM | top | top | top |
| 8 | top | top | top | NM | NM | top | top | top | top | top | NM | NM | top | top | top |
| 9 | 0 | 15.5 | 16.5 | NM | NM | 23 | top | top | top | top | NM | NM | top | top | top |
| 10 | top | top | top | NM | NM | top | top | top | top | top | NM | NM | top | top | top |

TABLE 3

| Col. # | Beginning Date | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|
| 1 | Aug. 26, 2003 | 0 | 68 | 0 | 25 | 0 | 0 | 247 | 61 | 75 | 34 | 0 | 103 | 43 | 39 |
| 2 | Aug. 26, 2003 | 0 | 201 | 0 | 55 | 0 | 0 | 234 | 199 | 108 | 68 | 0 | 163 | 44 | 23 |
| 3 | Aug. 26, 2003 | 0 | 106 | 0 | 41 | 0 | 0 | 153 | 63 | 54 | 43 | 0 | 69 | 33 | 25 |
| 4 | Aug. 26, 2003 | 0 | 184 | 0 | 30 | 0 | 0 | 121 | 46 | 85 | 39 | 0 | 98 | 28 | 14 |
| 5 | Aug. 26, 2003 | 0 | 124 | 0 | 57 | 0 | 0 | 138 | 18 | 21 | 16 | 0 | 22 | 8 | 2 |
| 6 | Aug. 26, 2003 | 0 | 114 | 0 | 15 | 0 | 0 | 19 | 0 | 0 | 0 | 0 | 0 | 0 | 0 |
| 7 | Aug. 26, 2003 | 0 | 0 | 0 | 0 | 0 | 116 | 0 | 0 | 0 | 0 | 0 | 0 | 0 | 0 |
| 8 | Aug. 26, 2003 | 0 | 53 | 0 | 12 | 0 | 0 | 11 | 2 | 0 | 3 | 0 | 1 | 0 | 0 |
| 9 | Aug. 26, 2003 | 0 | 2 | 0 | 0 | 1 | 2 | 0 | 1 | 0 | 0 | 10 | 2 | 0 | 0 |
| 10 | Aug. 26, 2003 | 0 | 42 | 0 | 2 | 0 | 0 | 3 | 2 | 2 | 2 | 0 | 1 | 0 | 0 |

| Col. # | Day 16 | Day 17 | Day 18 | Day 19 | Day 20 | Day 21 | Day 22 | Day 23 | Day 24 | Day 25 | Day 26 | Day 27 | Day 28 | Day 29 | Day 30 |
|---|---|---|---|---|---|---|---|---|---|---|---|---|---|---|---|
| 1 | 39 | 30 | 18 | NM | NM | 25 | 7 | 2 | 1 | 0 | NM | NM | NM | NM | 3 |
| 2 | 50 | 27 | 15 | NM | NM | 36 | 4 | 1 | 0 | 1 | NM | NM | NM | NM | 1 |
| 3 | 14 | 6 | 21 | NM | NM | 66 | 15 | 1 | 1 | 6 | NM | NM | NM | NM | 10 |
| 4 | 35 | 17 | 17 | NM | NM | 47 | 11 | 2 | 3 | 2 | NM | NM | NM | NM | 0 |
| 5 | 4 | 6 | 2 | NM | NM | 12 | 2 | 1 | 1 | 3 | NM | NM | NM | NM | 1 |
| 6 | 0 | 0 | 0 | NM | NM | 0 | 1 | 1 | 0 | 0 | NM | NM | NM | NM | 0 |
| 7 | 0 | 0 | 0 | NM | NM | 1 | 0 | 0 | 0 | 0 | NM | NM | NM | NM | 0 |
| 8 | 0 | 0 | 0 | NM | NM | 1 | 0 | 0 | 0 | 0 | NM | NM | NM | NM | 0 |
| 9 | 11 | 12 | 9 | NM | NM | 6 | 1 | 1 | 0 | 0 | NM | NM | NM | NM | 0 |
| 10 | 2 | 0 | 0 | NM | NM | 0 | 0 | 1 | 0 | 0 | NM | NM | NM | NM | 0 |

TABLE 4

| Sample ID | WT/Termite gm | Total WT gm | Initial Termites # | Live Workers # | Live Soldiers # | Mortality % | Weight loss % | Visual Rating 0-10 |
|---|---|---|---|---|---|---|---|---|
| 1 | 0.0046 | 9.223 | 2005 | 419 | 1 | 79.05% | NA | NA |
| 2 | 0.0046 | 9.224 | 2005 | 0 | 0 | 100.00% | NA | NA |
| 3 | 0.0046 | 9.211 | 2002 | 137 | 0 | 93.16% | NA | NA |
| 4 | 0.0046 | 9.226 | 2006 | 68 | 5 | 96.36% | NA | NA |
| 5 | 0.0046 | 9.241 | 2009 | 95 | 3 | 95.12% | NA | NA |
| Mean | 0.0046 | 9.225 | 2005.4 | 143.8 | 1.8 | 92.74% | | |
| St Dev | 0 | 0.011 | 2.3 | 161.7 | 2.2 | 0.08 | | |
| 6 | 0.0046 | 9.255 | 2012 | 1251 | 21 | 36.78% | NA | NA |
| 7 | 0.0043 | 8.58 | 1995 | 1250 | NA | 37.35% | NA | NA |
| 8 | 0.0046 | 9.243 | 2009 | 1011 | 9 | 49.24% | NA | NA |
| 9 | 0.0046 | 9.319 | 2026 | 1572 | 9 | 21.96% | NA | NA |
| 10 | 0.0046 | 9.264 | 2014 | 1316 | 28 | 33.26% | NA | NA |
| Mean | 0.0045 | 9.132 | 2011.3 | 1280.0 | 16.8 | 35.72% | | |
| St Dev | 0.0001 | 0.310 | 10.9 | 200.4 | 9.4 | 0.10 | | |
| C1 | 0.0046 | 1.841 | 400 | 336 | 7 | 14.30% | 44.60% | 0 |
| C2 | 0.0046 | 1.845 | 401 | 355 | 6 | 9.99% | 43.57% | 2 |
| C3 | 0.0046 | 1.847 | 402 | 351 | 5 | 11.34% | 44.23% | 2 |
| C4 | 0.0046 | 1.842 | 400 | 352 | 11 | 9.35% | 44.52% | 0 |
| C5 | 0.0046 | 1.848 | 402 | 312 | 6 | 20.84% | 41.57% | 0 |
| Mean | 0.0046 | 1.844 | 401.0 | 341.2 | 7.0 | 13.16% | 43.70% | 0.8 |
| St Dev | 0 | 0.003 | 0.7 | 17.9 | 2.3 | 0.05 | 1.26% | 1.10 |

While the present invention has been described with reference to several particular implementations, those skilled in the art will recognize that many changes may be made hereto without departing from the spirit and scope of the present invention.

We claim:

1. A man-made structure comprising:
   at least one non-wood building component having a first portion disposed adjacent ground or soil, a second portion vertically disposed above the ground or soil, and an above-ground surface which is susceptible to the formation of termite shelter tubes; and
   at least one wood or cellulosic building component disposed adjacent the second portion of the non-wood building component without being adjacent ground or soil;
   wherein the above-ground surface of the non-wood building component is coated with a borate solution consisting essentially of from about 10.0 weight percent to about 30.0 weight percent disodium octaborate tetrahydrate, and at least one glycol, and an aqueous solvent, and
   wherein the borate solution coating provides a termite barrier which is effective to substantially reduce termite tube formation across the surface of the non-wood building component, and
   wherein the at least one glycol is selected from the group consisting of propylene glycol, monoethylene glycol, diethylene glycol, triethylene glycol, polyethylene glycol, and mixtures thereof.

2. The man-made structure of claim 1, wherein the non-wood building component is cementitious.

3. The man-made structure of claim 1, wherein the non-wood building component is metal.

4. The man-made structure of claim 1, wherein the non-wood building component is polymeric.

5. The man-made structure of claim 1, wherein the surface of the non-wood building component is coated with an average coating of from about 0.0005 g/cm$^2$ to about 1.0 g/cm$^2$ of the borate solution.

6. The man-made structure of claim 1, the surface of the non-wood building component is coated with an average coating of from about 0.04 g/cm$^2$ to about 0.10 g/cm$^2$ of the borate solution.

7. The man-made structure of claim 1, wherein the borate solution coating provides a termite barrier which is effective to limit termite tube formation across the surface of the non-wood building component to a length of less than about 6 inches.

8. The man-made structure of claim 1, wherein the borate solution coating provides a termite barrier which is effective to limit termite tube formation across the surface of the non-wood building component to a length of less than about 12 inches.

9. The man-made structure of claim 1, wherein the borate solution coating provides a termite barrier which is effective to limit termite tube formation across the surface of the non-wood building component to a length of less than about 24 inches.

10. The man-made structure of claim 1, wherein the at least one non-wood building component comprises a foundation wall.

* * * * *